(12) United States Patent
Kilbey

(10) Patent No.: US 9,463,109 B2
(45) Date of Patent: Oct. 11, 2016

(54) WRIST ORTHOTIC WITH TAPER ADJUSTING BINDING STRAP

(71) Applicant: Bryan E. Kilbey, DeFuniak Sprs, FL (US)

(72) Inventor: Bryan E. Kilbey, DeFuniak Sprs, FL (US)

( * ) Notice: Subject to any disclaimer, the term of this patent is extended or adjusted under 35 U.S.C. 154(b) by 741 days.

(21) Appl. No.: 13/886,359

(22) Filed: May 3, 2013

(65) Prior Publication Data

US 2014/0330189 A1 Nov. 6, 2014

(51) Int. Cl.
*A61F 5/00* (2006.01)
*A61F 5/058* (2006.01)
*A61F 5/01* (2006.01)

(52) U.S. Cl.
CPC .......... *A61F 5/05866* (2013.01); *A61F 5/0118* (2013.01)

(58) Field of Classification Search
CPC .......... A61F 5/00; A61F 5/01; A61F 5/0102; A61F 5/0104; A61F 5/0118; A61F 5/013; A61F 5/04; A61F 5/05; A61F 5/058; A61F 5/05841; A61F 5/05858; A61F 5/05866
USPC ...... 2/16, 162, 166; 128/846, 869, 878, 879, 128/880; 602/5, 20–22, 60–64
See application file for complete search history.

(56) References Cited

U.S. PATENT DOCUMENTS

| | | | | |
|---|---|---|---|---|
| 4,854,309 A * | 8/1989 | Elsey | ................. | A61F 5/0118 602/21 |
| 5,415,624 A * | 5/1995 | Williams | .............. | A61F 5/0104 602/14 |
| 5,769,804 A * | 6/1998 | Harris | .................. | A61F 5/0118 602/20 |
| 6,024,715 A * | 2/2000 | Maxwell | .............. | A61F 5/0118 602/21 |
| 6,146,348 A * | 11/2000 | Slautterback | ....... | A61F 5/05866 602/21 |
| 6,200,286 B1 * | 3/2001 | Zamani | ................. | A61F 5/0118 602/20 |
| 6,730,053 B1 * | 5/2004 | Bodenschatz | ......... | A61F 5/0118 128/878 |
| 6,960,176 B1 * | 11/2005 | Hely | ..................... | A61F 13/108 602/20 |
| 7,056,298 B1 * | 6/2006 | Weber | .................. | A61F 5/0118 2/16 |
| 8,114,041 B2 * | 2/2012 | Wyatt | .................. | A61F 5/0118 128/846 |
| 8,388,563 B2 * | 3/2013 | Jaccard | ................. | A61F 5/0118 128/878 |
| 2013/0211304 A1 * | 8/2013 | Romo | ................... | A61F 5/0118 602/21 |

* cited by examiner

*Primary Examiner* — Michael Brown
(74) *Attorney, Agent, or Firm* — J. Wiley Horton

(57) ABSTRACT

An adjustable wrist orthotic suitable for the treatment of wrist fractures and similar injuries. The orthotic includes a panel which encircles the hand, the wrist, and a portion of the forearm. An adjustment break is included to allow the adjustment of the circumference of the orthotic. The adjustment break is selectively closed and secured using a plurality of straps secured by VELCRO or other suitable fasteners. Each strap begins on one side of the adjustment break, then passes through a strap ring on the opposite side of the adjustment break, then loops back over itself. Each strap is secured by pressing the looped portion back on the strap itself. The VELCRO then engages to secure the strap in place. A 4-way elastic panel is included in the anchor point of a securing strap. This 4-way panel allows the strap to bend laterally in order to accommodate variations in forearm taper.

20 Claims, 9 Drawing Sheets

WRIST ORTHOTIC WITH TAPER ADJUSTING BINDING STRAP

CROSS-REFERENCES TO RELATED APPLICATIONS

This application is a non-provisional application claiming priority to U.S. Provisional Application No. 61/642,477 filed on May 4, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises a wrist orthotic including a binding strap which conforms to a variable amount of taper in a patient's forearm anatomy.

2. Description of the Related Art

Wrist fractures were traditionally placed in plaster casts in order to immobilize the affected anatomy. In recent years, more flexible orthotic devices have replaced the plaster casts. These usually encircle the wrist and palm with fabric material. One or more rigid, stays are incorporated in the device in order to provide the requisite rigidity.

Elastic panels are used to adapt the orthotic to a range of sizes. Adjustable securing straps also aid proper fitting of the device. However, the geometry of the wrist and forearm varies widely from individual to individual. Prior art devices have been able to accommodate variations in wrist and forearm diameter fairly well. They have not done as well, though, in accommodating variations in the taper of a patient's forearm. This is particularly true for a long wrist orthotic which may extend nearly to a patient's elbow.

A muscular, stocky patient has a forearm which expands rapidly, whereas a thin patient may have little to no expansion. The traditional solution to this concern has been to provide multiple wrist orthotics having varying geometry. This is a wasteful approach. It would therefore be advantageous to provide a single wrist orthotic which could accommodate a wide variation in forearm geometry.

BRIEF SUMMARY OF THE PRESENT INVENTION

The present invention comprises an adjustable wrist orthotic suitable for the treatment of wrist fractures and similar injuries. The orthotic includes a panel which encircles the hand, the wrist, and a portion of the forearm. An adjustment break is included to allow the adjustment of the circumference of the orthotic. The adjustment break is selectively closed and secured using a plurality of straps secured by VELCRO or other suitable fasteners. Each strap begins on one side of the adjustment break, then passes through a strap ring on the opposite side of the adjustment break, then loops back over itself. Each strap is secured by pressing the looped portion back on the strap itself. The VELCRO then engages to secure the strap in place.

If the two sides of the adjustment break are parallel, then the straps will lie flat when they are looped through the strap rings and pressed into the secured position. However, if the patient's forearm is significantly tapered, the adjustment break will not be parallel but will instead diverge significantly when proceeding in the direction toward the elbow. In this case the straps will not tend to lie flat because they are essentially lying on a conical surface rather than a cylindrical one. This is particularly true for the strap closest to the elbow. One side of this strap will tend to bulge outward. The bulge may snag on obstacles and clothing, which is a significant problem.

The present invention solves this problem by including a 4-way elastic panel in the anchored portion of a securing strap. This 4-way panel allows the strap to bend laterally in order to accommodate variations in forearm taper.

Figure 1:
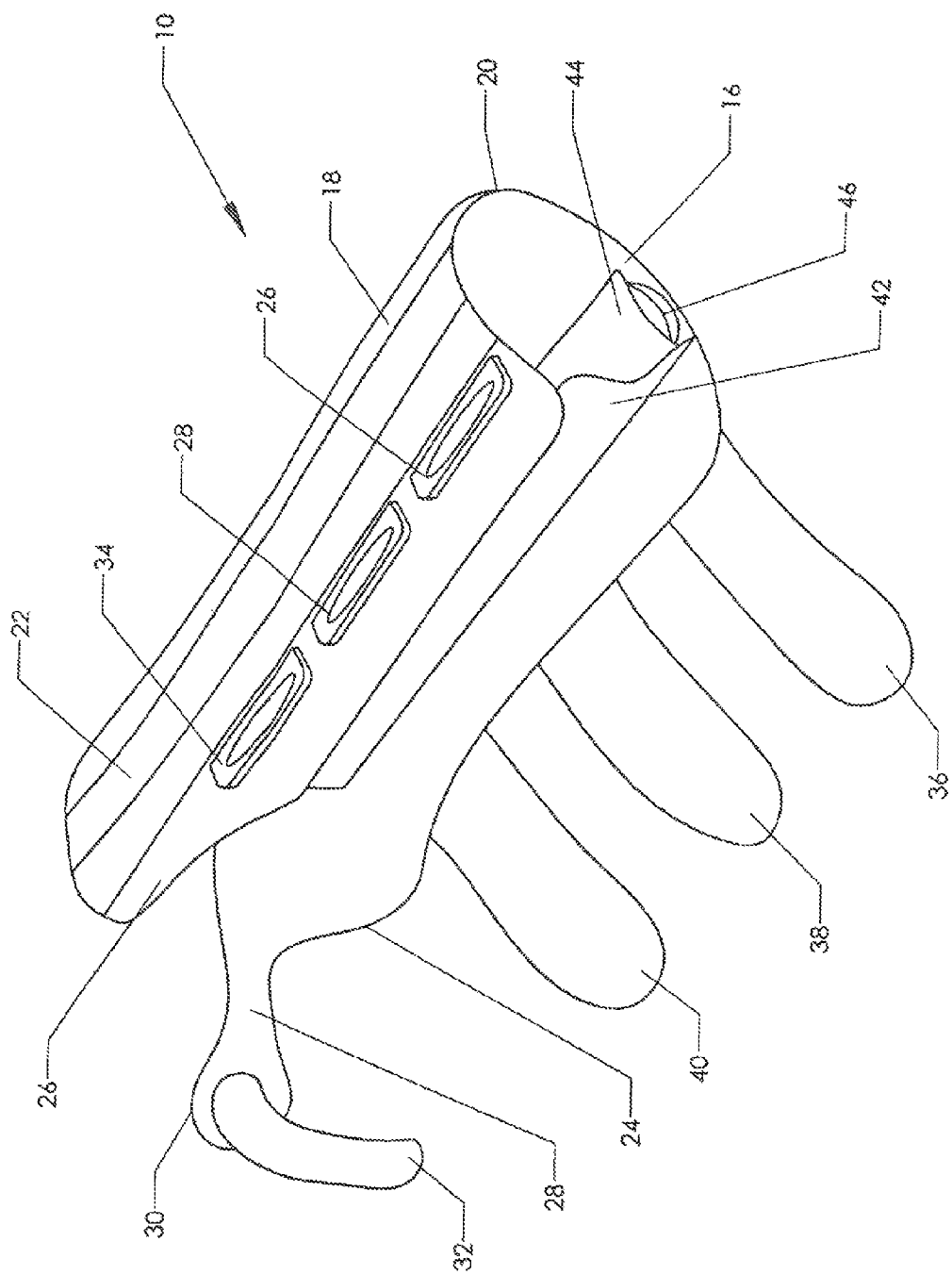
FIG. 1 is a perspective view, showing a wrist splint made according to the present invention.

| REFERENCE NUMERALS IN THE DRAWINGS | | | |
|---|---|---|---|
| 10 | wrist splint | 16 | bottom panel |
| 18 | top panel | 20 | side panel |
| 22 | loop panel | 24 | bottom thumb relief |
| 25 | first strap ring | 26 | top thumb relief |
| 27 | second strap ring | 28 | thumb strap |
| 30 | tab | 32 | hook panel |
| 32 | hook panel | 34 | third strap ring |
| 36 | first strap | 38 | second strap |
| 40 | third strap | 42 | radius panel |
| 44 | stay pocket | 46 | stay |
| 48 | first anchor | 50 | second anchor |
| 52 | third anchor | 54 | hook loop covering |
| 56 | stay | 58 | central passage |
| 60 | 4-way elastic panel | 62 | stay pocket |
| 78 | forearm | 80 | divergence angle |
| 82 | hand end | 84 | forearm end |
| 86 | cylinder | 88 | cone |
| 90 | tape | 92 | cant angle |
| 94 | adjustment break | | |

DETAILED DESCRIPTION OF THE INVENTION

FIG. 1 shows wrist splint 10. It includes top panel 18, side panel 20, and bottom panel 16. The top ad bottom panel may be separate pieces. In other embodiments the top, bottom, and side pieces may be formed as one continuous encircling band. Whatever construction is employed, an adjustment break 94 is left open between the side of the top and bottom panels lying next to the user's thumb when the splint is installed. This adjustment break allows the diameter and the taper of the splint to the adjusted to accommodate variations in patient anatomy.

One or more straps and strap rings are provided to secure the device in position. First strap ring 25, second strap ring 27, and third strap ring 34 are attached to top panel 18 near a first side of adjustment break 94. First strap 36, second strap 38, and third strap 40 are secured to the bottom or side panels on a second side of adjustment break 94. The straps are passed through the strap rings and secured in place—as will be described subsequently.

The end of the wrist splint intended to lie over a portion of the patient's hand includes top thumb relief 26 and bottom thumb relief 24. These allow the patients thumb to lie outside the brace. Thumb strap 28 is positioned to pass between the patients thumb and first finger before being fastened back to the rest of the splint. In the embodiment shown, thumb strap 28 is part of the bottom panel. A fastening device is provided to attach its free end to the top panel. In the embodiment shown, hook panel 3 is positioned to engage loop panel 22 (VELCRO-type fasteners) on top panel 18. Tab 30 is provided so that the patient may easily disengage the thumb strap when removing the splint. The user may grasp tab 30 between the thumb and forefinger of the opposite hand and pull the thumb strap free.

The wrist splint preferably includes rigid or semi-rigid stays to stabilize the patient's anatomy in a desired orientation. Stay pocket 44 includes a removable stay 46. The stays are preferably made removable so that a greater range of motion can be provided by removing one or more stays as the patient heals.

Radius panel 42 is preferably provided between top panel 18 and bottom panel 16 across adjustment break 94. The radius panel is preferably made of elastic material. It retains the general shape of the wrist splint while the straps are disconnected—thereby allowing the user to more easily install the splint.

Figure 2:
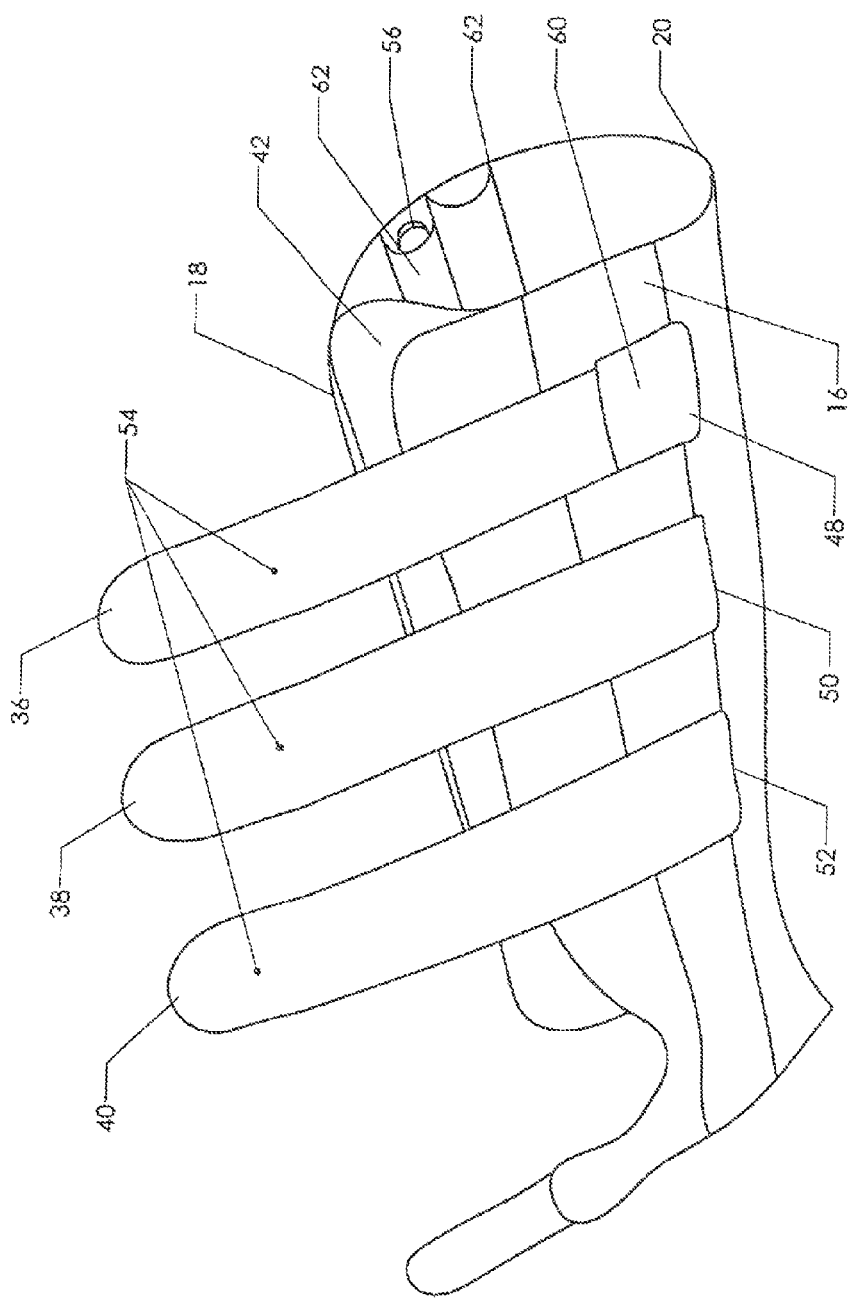
FIG. 2 is a perspective view, showing the wrist splint of FIG. 1 from another perspective.

FIG. 2 shows the wrist splint from a different vantage point (looking toward bottom panel 16). The three straps are connected to the encircling band of the wrist splint on the opposite side of the adjustment break than the strap rings. In the embodiment shown, first strap 36 is attached to the bottom panel 16 via 4-way elastic panel 60. The elastic panel is a rectangular piece of material capable of stretching in 4 directions. In other words, each side of the rectangle may expand differently—yet the panel as a whole will remain flat. The first end of 4-way elastic panel 60 is connected to bottom panel 16 at first anchor 48. The second end of the elastic panel is connected to the first end of first strap 36. The second end of first strap 36 is free.

The term "anchor" means any suitable attachment between a strap (or elastic panel) and the balance of the wrist splint. A suitable approach to creating such an attachment includes stitching, gluing, riveting, etc. The straps are anchored to the encircling band on the opposite side of the adjustment break from the strap rings. The distance between the anchors and the adjustment break may be widely varied.

Additional straps may or may not include a 4-way elastic panel 60. In the example shown, second strap 38 is directly connected to bottom panel 16 at second anchor 50. Likewise, third strap 40 is directly connected to bottom panel 16 at third anchor 52.

The surface of each of the straps facing the user in FIG. 2 is covered with a VELCRO fastening material. This is ideally a combination hook and loop material so that each strap can be threaded through a strap eye, then pressed back upon itself to secure it in place (in much the same manner as VELCRO shoe closures).

FIG. 2 also shows how top panel 8 preferably includes one or more stay pocket 62. These pockets optionally contain additional stays 56. As for the bottom panels, the stays are preferably made removable.

Figure 3:
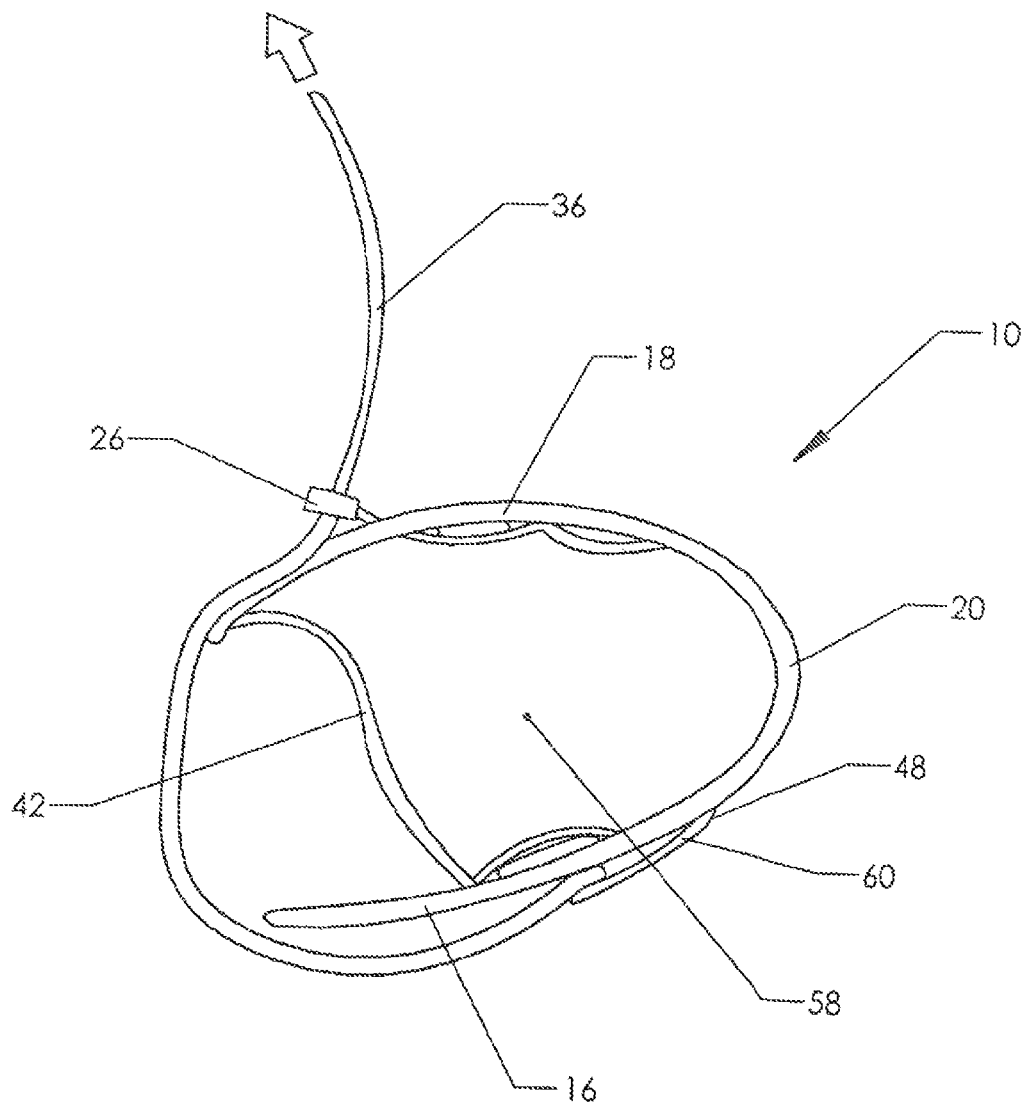
FIG. 3 is an elevation view, showing the path taken by the securing straps

FIG. 3 shows a simplified end elevation view of the wrist splint. The reader will observe how top panel 18, side panel 20, and bottom panel 16 combine to form an encircling band. Radius panel 42 spans the adjustment break, thereby defining central passage 58. The user slips the wrist splint over the hand, wrist and forearm by passing that anatomy through central passage 58.

Radius panel 42 is long enough to allow the wrist splint to suitably expand during installation (and may in fact be made of elastic material). During the installation process, the tip of first strap 36 is passed through first strap ring 25 as indicated by the arrow. The strap is then pulled taut to adjust the diameter of the wrist splint. Pulling the strap taut causes 4-way elastic panel 60—as well as the strap itself—to lie flat against the encircling band of the wrist splint.

Figure 4:
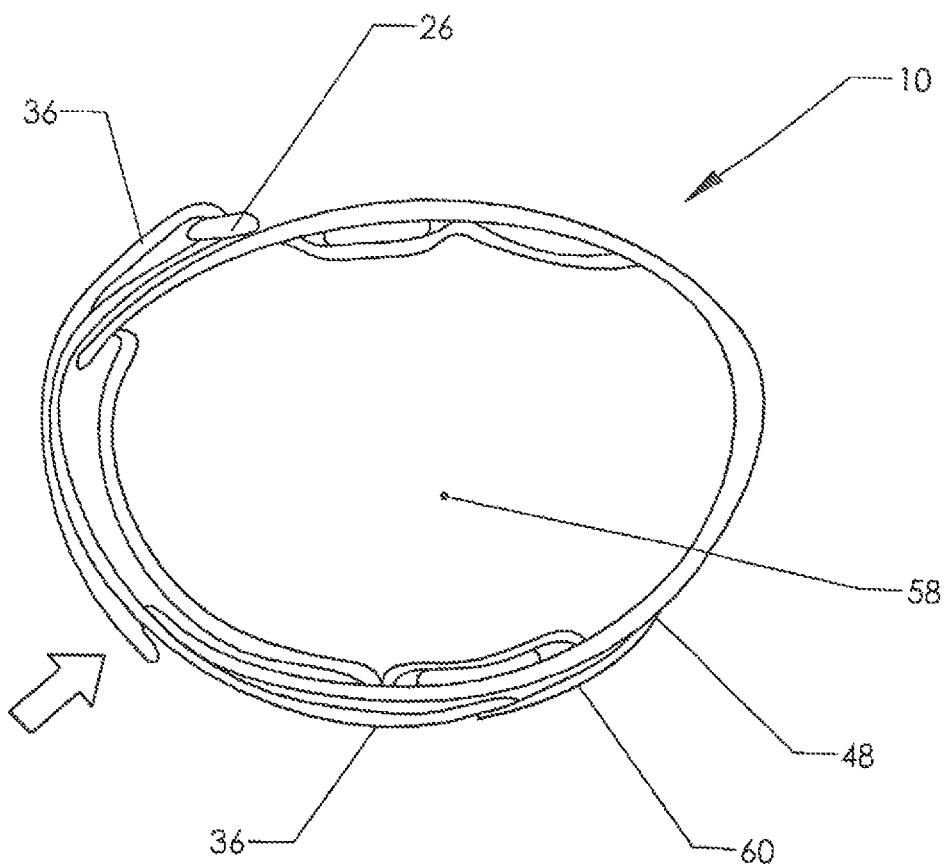
FIG. 4 is an elevation view, showing the straps in a secured position.

In FIG. 4 first strap 36 has been pulled to create the desired level of tension and then pressed back onto itself to secure it in place. The hook/loop material on the strap secures it in the desired position. The reader will note how 4-way elastic panel 60 and first strap 36 lie flat against the encircling band.

Figure 5:
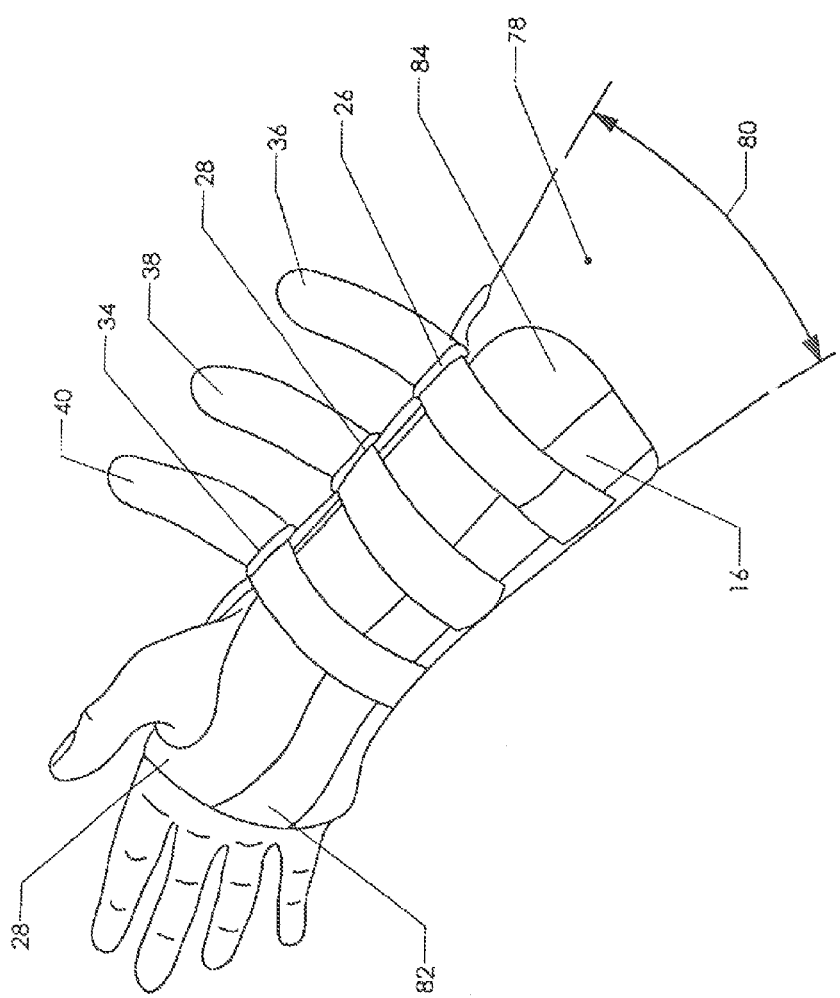
FIG. 5 is a perspective view, showing the wrist splint being installed on a patient.

The inclusion of one or more 4-way elastic panels is a significant advantage in the present invention, as it allows the accommodation of variable patient forearm geometry. FIG. 5 shows the wrist splint being installed on a patient. The encircling band has a forearm end lying near the patient's forearm 78 and a hand end 82 lying near the patient's hand. Thumb strap 28 is secured around the thumb as shown. First strap 36 is passed through first strap ring 25. Second strap 38 is passed through second strap ring 27. Third strap 40 is passed through third strap ring 34. The straps may in fact be left in this position as the device is applied and removed.

Figure 6:
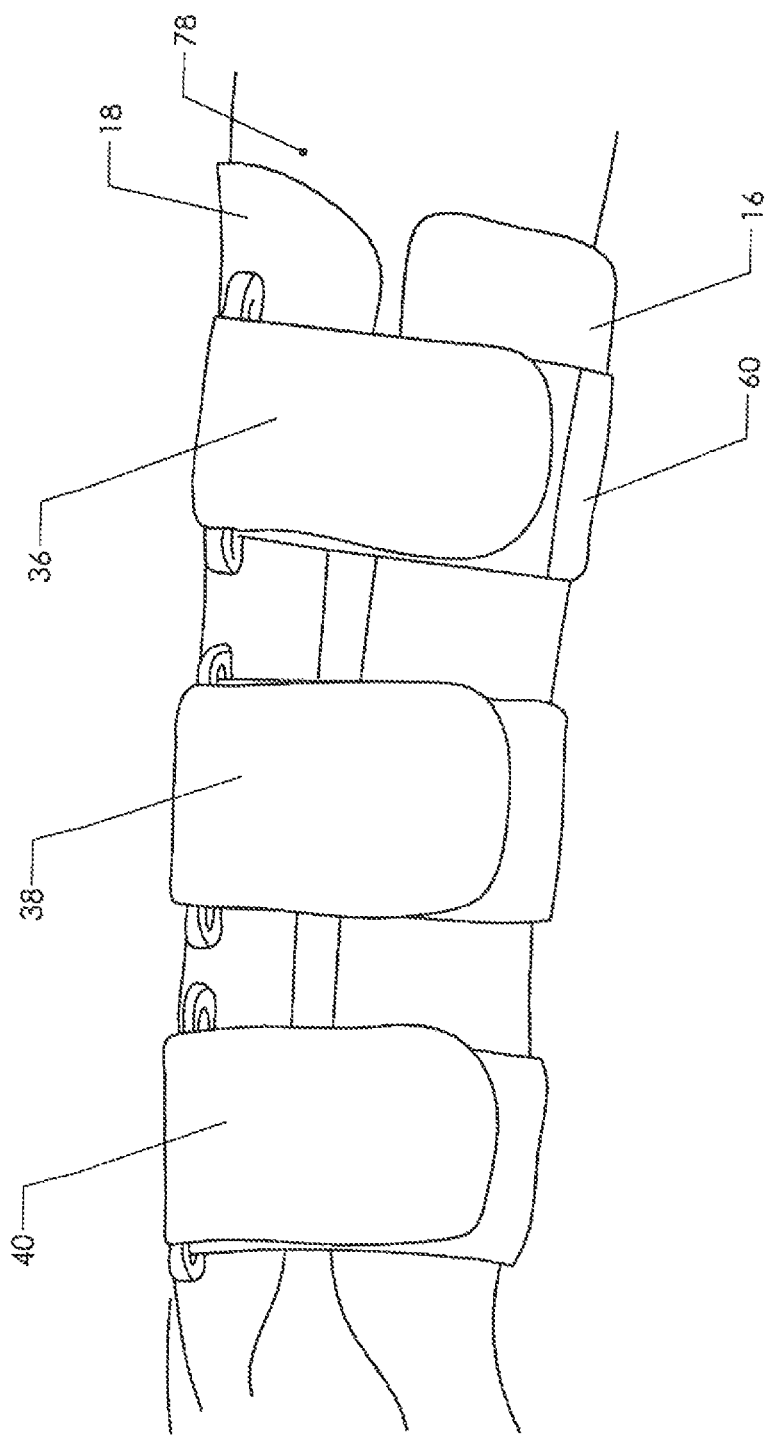
FIG. 6 is a side elevation view, showing the securing straps in a case where the adjustment break is parallel.

The patient's forearm in this example has a large divergence angle 80. This presents an issue for adequately adjusting the wrist splint, as will be explained. FIG. 6 shows the application of the Wrist splint to a patient having little to no divergence in the forearm. The reader will observe how the two sides of adjustable break 94 are nearly parallel. The encircling band is essentially cylindrical in this configuration, which makes the three straps lie flat. 4-way elastic panel 60 does stretch somewhat under tension but it does not deviate laterally.

Figure 7:
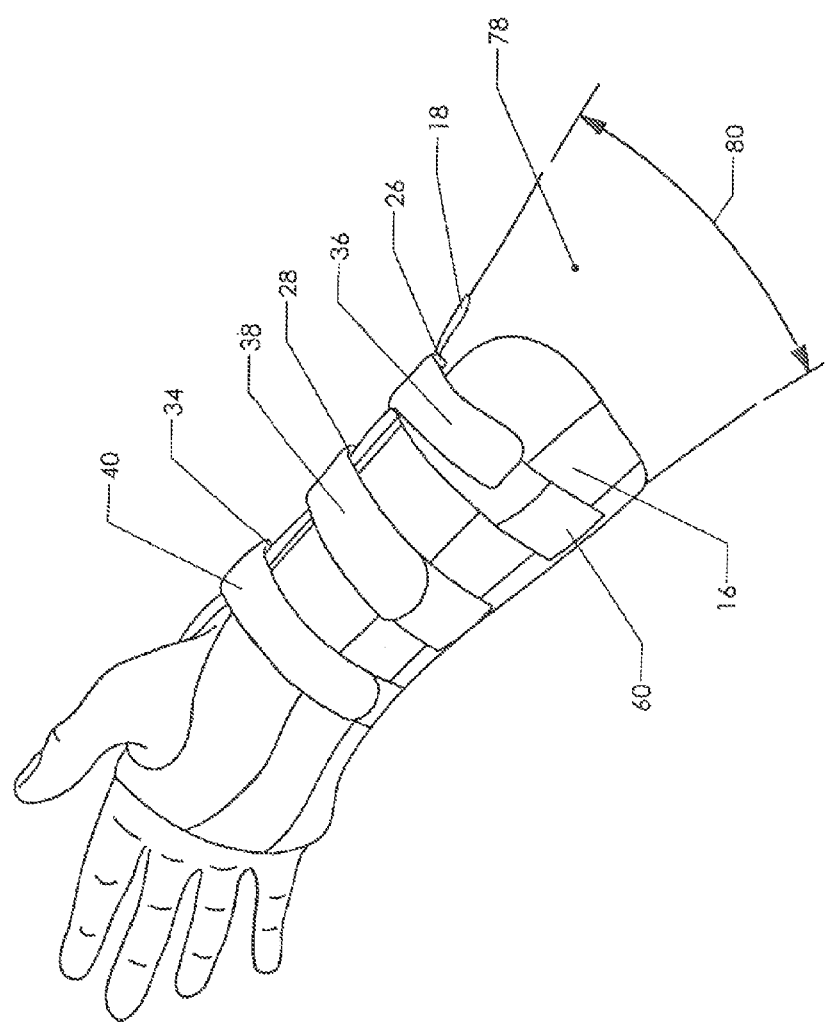
FIG. 7 is a perspective view, showing the use of a 4-way elastic panel in the anchor of one of the securing straps.

In contrast, FIG. 7 shows the wrist splint installed on a patient with a large divergence angle 80 in the forearm. The presence of 4-way elastic panel 60 allows first strap 36 to deflect laterally as shown. This allows the third strap to lie flat against the wrist splint rather than having a portion which bulges outward.

Figure 8:
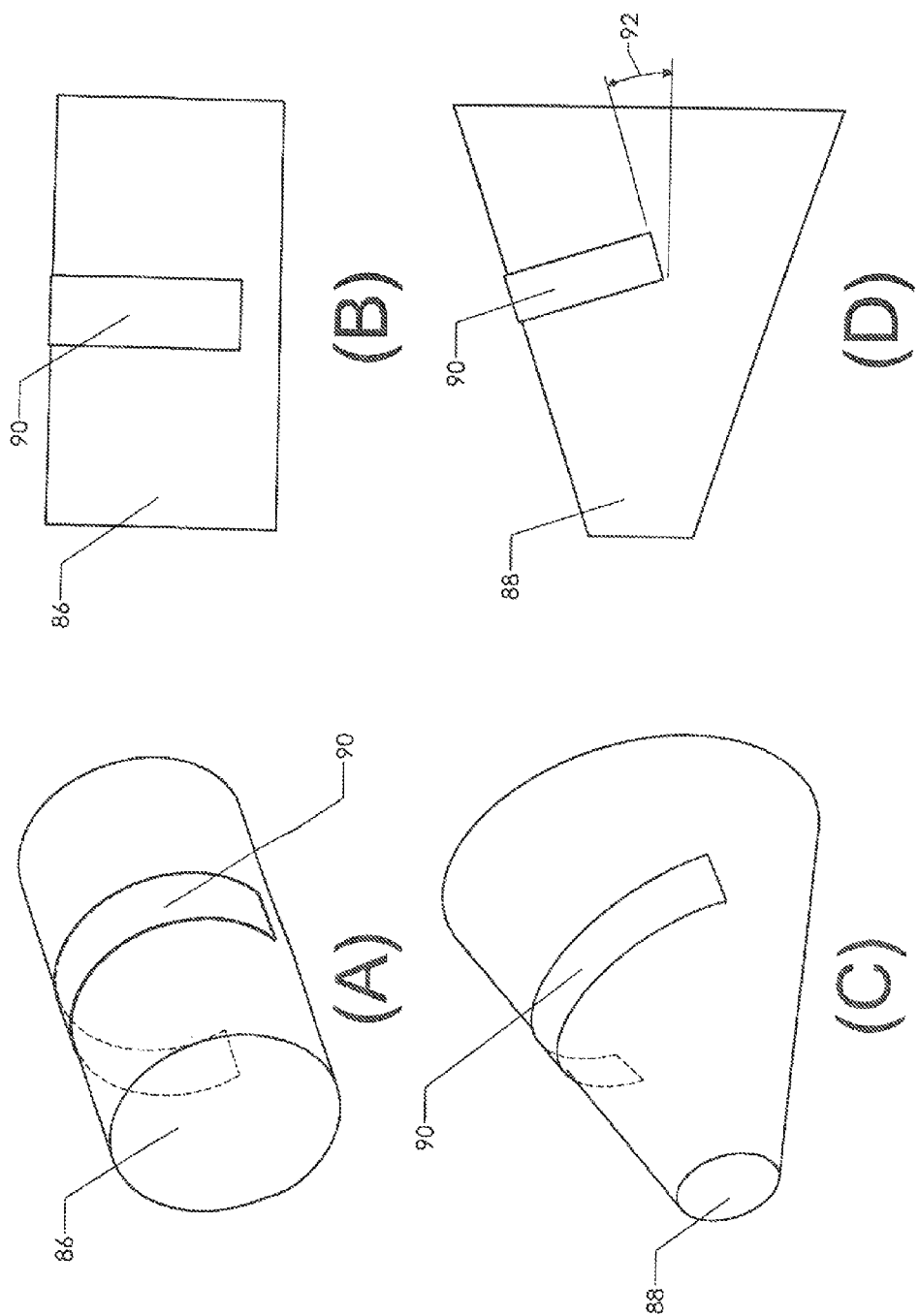
FIG. 8 is a perspective view, illustrating how a strap lies on a cylindrical surface versus a conical one.

The reason for this phenomenon may be difficult to perceive from the study of two-dimensional drawings, so FIG. 8 is provided to simplify the phenomenon so that it may be more easily understood. FIGS. 8(a) and (b) show a simple cylinder 86. FIG. 8(a) shows a perspective view of a length of tape 90 that is affixed to the surface of the cylinder in an orientation which is perpendicular to the central axis of the cylinder.

FIG. 8(b) shows a side elevation view of the same assembly. The reader will observe how tape 90 lies flat on the cylindrical surface. FIGS. 8(*c*) and (*d*), however, depict a truncated cone 88. Tape 90 cannot lie flat on the conical surface if its orientation is perpendicular to the central axis of the cone. FIG. 8(*d*) shows a side elevation view of cone 88 with tape 90 attached. The reader will observe how the orientation of tape 90 must be offset by cant angle 92 in order to lie flat. Still looking at FIG. 8(*d*), those skilled in the art will appreciate that if the tape is applied in an orientation which is perpendicular to the central axis of the cone, one edge of the tape will lie on the conical surface and the second end will lie well above the conical surface.

The same thing happens when the straps are secured around the wrist splint. Returning to FIG. 7, the anatomy of the patient's wrist and forearm in the vicinity of second strap 38 and third strap 40 is roughly cylindrical. Thus, conventional securing straps may be used. However, in the vicinity of first strap 36, the forearm is rapidly expanding and has a surface which is roughly conical. The encircling band of the wrist splint therefore assumes a conical shape on this region.

Figure 9:
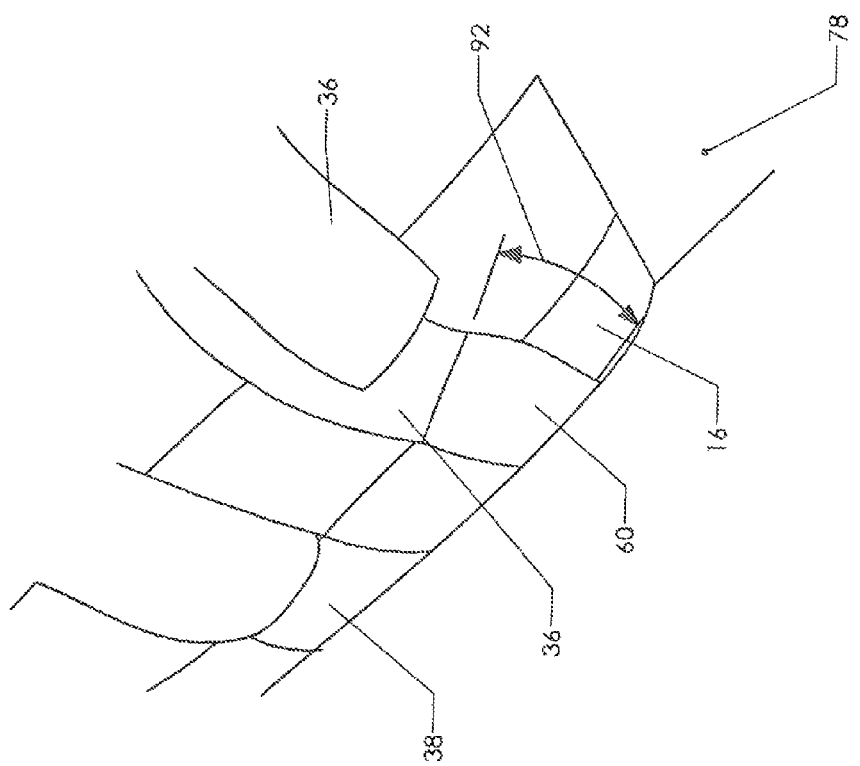
FIG. 9 is a detailed perspective view, showing the use of a 4-way elastic panel to create a desired cant angle for a securing strap.

4-way elastic panel 60 allows first strap 36 to laterally offset in a manner analogous to the tape in FIG. 8(*d*). FIG. 9 shows a detailed view of 4-way elastic panel 60 in the same configuration as shown in FIG. 7. The elastic panel has allowed first strap 36 to offset laterally through cant angle 92, which has allowed the entire strap to lie flat against the surface of the encircling band. Without this feature, the edge of first strap 36 closest to the patient's hand would bulge outward and produce a snag hazard. The fact that the elastic panel can stretch a variable amount along all four edges means that no portion of the elastic panel itself bulges outward.

The cant angle may vary as needed. For a person with a small forearm, the cant angle may even be zero. The use of the 4-way elastic panel allows all these variations to be accommodated.

The embodiment shown in FIG. 7 discloses the use of only one 4-way elastic panel on the strap closest to the patient's elbow. In other embodiments, additional 4-way elastic panels may be provided on second strap 38 and/or third strap 40. It is also possible to provide embodiments with only two straps—as well as four or more straps.

Although the preceding description contains significant detail, it should not be viewed as limiting the invention but instead as providing illustrations of the preferred embodiments of the invention. Many other alterations could be made to the embodiments illustrated without altering the substance of the invention. As an example, buckle connections could be made between the securing straps and the encircling band rather than using VELCRO. Thus, the scope of the present invention should be defined by the following claims rather than any specific examples given.

Having described my invention, I claim:

1. A wrist splint for stabilizing the anatomy of a patient's hand, wrist, and forearm, comprising:
    a. a top panel having a hand end and a forearm end;
    b. a bottom panel having a hand end and a forearm end, said bottom panel being separated from said top panel by an adjustment break;
    c. at least one strap ring located on said top panel;
    d. at least one strap, having a first end and a second end;
    e. a 4-way elastic panel, having a first end and a second end, with said first end of said 4-way elastic panel being attached to said bottom panel at an anchor;
    f. said first end of said at least one strap being attached to said second end of said 4-way elastic panel, said 4-way elastic panel is attached to said strap to angularly deflect and form a suitable cant angle between said anchor and said at least one strap while said 4-way elastic panel and said at least one strap remain flat; and
    g. said at least one strap being configured to pass through said at least one strap ring and then secure back to itself.

2. A wrist splint as recited in claim 1, further comprising:
    a. a thumb strap proximate said hand end of said bottom panel;
    b. a hook-and-loop panel on said upper panel; and
    c. a hook-and-loop panel on said thumb strap, positioned so that said hook-and-loop panel on said thumb strap engages said hook-and-loop panel on said upper panel when said thumb strap is placed over said patient's hand.

3. A wrist splint as recited in claim 2, wherein said thumb strap includes a tab positioned to be pulled in order to disengage said thumb strap from said upper panel.

4. A wrist splint as recited in claim 1, further comprising a radius panel spanning said adjustment break.

5. A wrist splint as recited in claim 1, further comprising a stay pocket in said bottom panel with a first stay contained within said stay pocket in said bottom panel.

6. A wrist splint as recited in claim 5, further comprising a stay pocket in said upper panel with a second stay contained within said stay pocket in said upper panel.

7. A wrist splint as recited in claim 1, further comprising:
    a. a second strap ring located on said top panel;
    b. a second strap, having a first end and a second end; and
    c. said first end of said second strap being attached to said bottom panel at a second anchor.

8. A wrist splint as recited in claim 7, further comprising:
    a. a third strap ring located on said top panel;
    b. a third strap, having a first end and a second end; and
    c. said first end of said third strap being attached to said bottom panel at a third anchor.

9. A wrist splint as recited in claim 1, wherein said top panel and said bottom panel are formed as one piece.

10. A wrist splint as recited in claim 7, wherein said top panel and said bottom panel are formed as one piece.

11. A wrist splint for stabilizing the anatomy of a patient's hand, wrist, and forearm, comprising:
    a. an encircling band having a hand end and a forearm end, said encircling band being long enough to cover a portion of said hand, said wrist, and a portion of said forearm;
    b. an adjustment break in said encircling band, said adjustment break having a first side and a second side;
    c. a strap ring located on said first side of said adjustment break;
    d. a strap, having a first end and a second end;
    e. a 4-way elastic panel, having a first end and a second end, with said first end of said 4-way elastic panel being attached to said encircling band on said second side of said adjustment break;
    f. said first end of said strap being attached to said second end of said 4-way elastic panel, said 4-way elastic panel is attached to said strap to angularly deflect and form a suitable cant angle between said anchor and said strap while said 4-way elastic panel and said strap remain flat; and
    g. said strap being configured to pass through said at least one strap ring and then secure back to itself.

12. A wrist splint as recited in claim 11, further comprising:
    a. a thumb strap proximate said hand end of said encircling band;
    b. a hook-and-loop panel on said encircling band; and c. a hook-and-loop panel on said thumb strap, positioned so that said hook-and-loop panel on said thumb strap engages said hook-and-loop panel on said encircling band when said thumb strap is placed over said patient's hand.

13. A wrist splint as recited in claim 12, wherein said thumb strap includes a tab positioned to be pulled in order to disengage said thumb strap from said encircling band.

14. A wrist splint as recited in claim 11, further comprising a radius panel spanning said adjustment break.

15. A wrist splint as recited in claim 11, further comprising a first stay pocket in said encircling band with a first stay contained within said first stay pocket.

16. A wrist splint as recited in claim 15, further comprising a second stay pocket in said encircling band with a second stay contained within said second stay pocket.

17. A wrist splint as recited in claim 11, further comprising:
 a. a second strap ring located on said first side of said adjustment break;
 b. a second strap, having a first end and a second end; and
 c. said first end of said second strap being attached to said encircling band at a second anchor.

18. A wrist splint as recited in claim 17, further comprising:
 a. a third strap ring located on said first side of said adjustment break;
 b. a third strap, having a first end and a second end; and
 c. said first end of said third strap being attached to said encircling band at a third anchor.

19. A wrist splint as recited in claim 11, wherein said encircling band is formed as one integral piece.

20. A wrist splint as recited in claim 17, wherein said encircling band is formed as one integral piece.

* * * * *